United States Patent
Ross et al.

(10) Patent No.: US 8,376,983 B2
(45) Date of Patent: Feb. 19, 2013

(54) METHOD FOR ASPIRATING FLUID UTILIZING A DUAL CYLINDER VACUUM PUMP

(75) Inventors: Rodney L. Ross, Mission Viejo, CA (US); Gregg Hughes, Mission Viejo, CA (US)

(73) Assignee: Enlighten Technologies, Inc., Laguna Hills, CA (US)

( * ) Notice: Subject to any disclaimer, the term of this patent is extended or adjusted under 35 U.S.C. 154(b) by 166 days.

(21) Appl. No.: 13/036,955

(22) Filed: Feb. 28, 2011

(65) Prior Publication Data
US 2011/0196320 A1 Aug. 11, 2011

Related U.S. Application Data

(62) Division of application No. 11/088,318, filed on Mar. 23, 2005, now abandoned.

(60) Provisional application No. 60/556,963, filed on Mar. 26, 2004.

(51) Int. Cl.
*A61M 1/00* (2006.01)
*A61M 5/00* (2006.01)
*A61M 31/00* (2006.01)
*F04B 41/06* (2006.01)
*F04B 23/04* (2006.01)
*F04B 43/12* (2006.01)
*F04B 17/00* (2006.01)

(52) U.S. Cl. ............ 604/35; 604/30; 604/151; 604/249; 604/521; 417/3; 417/62; 417/53; 417/339

(58) Field of Classification Search ............. 604/521, 604/249, 30, 35, 131; 417/6, 339, 44.2, 44.3, 417/521, 2, 32, 53
See application file for complete search history.

(56) References Cited

U.S. PATENT DOCUMENTS

| 805,530 A | 11/1905 | Davis |
| 1,267,088 A | 5/1918 | Lane |

(Continued)

FOREIGN PATENT DOCUMENTS

| EP | 0 484 050 A1 | 5/1992 |
| JP | 2008-121326 | 5/2008 |

(Continued)

OTHER PUBLICATIONS

International Search Report and Written Opinion From Corresponding PCT Application No. PCT/US05/09666, Jun. 11, 2008 (10 pgs).

*Primary Examiner* — Kevin C Sirmons
*Assistant Examiner* — Bradley G Thomas, Jr.
(74) *Attorney, Agent, or Firm* — The Eclipse Group LLP; David P. Gloekler

(57) ABSTRACT

Irrigation fluid is aspirated from an eye and through an aspiration instrument by operating a vacuum pump, including moving first and second plungers between respective suction strokes and discharge strokes. Vacuum pressure at an input side of the pump is maintained at a desired vacuum pressure setting by controlling speeds and directions of the plungers, and controlling positions of input and output valves communicating with cylinders in which the plungers move. Controlling is based on the pressure setting and measured pressures in the cylinders. Vacuum pressure is maintained while transitioning from the suction stroke of the first plunger to the suction stroke of the second plunger, by synchronizing respective positions of the plungers and the valves, such that initiation of the suction stroke of the second plunger during the transitioning is delayed until a vacuum pressure in the second cylinder is equal to a vacuum pressure in the first cylinder.

15 Claims, 2 Drawing Sheets

U.S. PATENT DOCUMENTS

| | | | |
|---|---|---|---|
| 3,597,113 A * | 8/1971 | Dumoulin et al. | 417/53 |
| 3,637,330 A | 1/1972 | Goeldner | 417/389 |
| 3,981,620 A | 9/1976 | Abrahams et al. | 417/42 |
| 4,127,360 A | 11/1978 | Carpenter | 417/5 |
| 4,273,261 A | 6/1981 | Krueger | 222/135 |
| 4,543,044 A | 9/1985 | Simmons | 417/342 |
| 4,734,187 A | 3/1988 | Visentin et al. | 210/101 |
| 4,808,077 A | 2/1989 | Kan et al. | 417/2 |
| 5,026,255 A | 6/1991 | Carpenter et al. | 417/5 |
| 5,206,255 A | 4/1993 | Ubasawa et al. | 514/374 |
| 5,492,535 A | 2/1996 | Reed et al. | 604/152 |
| 5,529,463 A | 6/1996 | Layer et al. | 417/403 |
| 5,630,706 A * | 5/1997 | Yang | 417/3 |
| 6,083,195 A * | 7/2000 | Perkins et al. | 604/30 |
| 6,113,368 A | 9/2000 | Hofmann | 417/539 |
| 6,264,442 B1 | 7/2001 | Foss | 417/515 |
| 6,368,080 B1 | 4/2002 | Sipin | 417/415 |
| 6,511,454 B1 | 1/2003 | Nakao et al. | 604/31 |
| 6,676,644 B2 | 1/2004 | Ikeda | 604/317 |
| 6,786,885 B2 | 9/2004 | Hochman et al. | 604/67 |
| 7,080,792 B2 | 7/2006 | Muratsubaki et al. | 239/67 |
| 7,278,836 B2 | 10/2007 | Hammonds | 417/515 |
| 2001/0016708 A1 | 8/2001 | Kong et al. | 604/152 |
| 2002/0151835 A1 * | 10/2002 | Ross | 604/22 |
| 2007/0129680 A1 | 6/2007 | Hagg et al. | 604/151 |

FOREIGN PATENT DOCUMENTS

WO   WO 2005/034777 A1   4/2005

* cited by examiner

METHOD FOR ASPIRATING FLUID UTILIZING A DUAL CYLINDER VACUUM PUMP

RELATED APPLICATIONS

This application claims the benefit of U.S. patent application Ser. No. 11/088,318, filed Mar. 23, 2005, titled "DUAL CYLINDER VACUUM PUMP FOR MEDICAL ASPIRATION SYSTEM," which claims the benefit of U.S. Provisional Patent Application Ser. No. 60/556,963, filed Mar. 26, 2004, titled "VACUUM PUMP", which are both incorporated by reference herein in their entirety.

TECHNICAL FIELD

The present invention relates to a vacuum pump for a medical aspiration system and a method for aspirating fluid utilizing the vacuum pump.

BACKGROUND

Ophthalmic procedures are typically performed with instruments that have a tip located at the distal end of a handpiece. The handpiece is held by a surgeon who inserts the tip into the inner ocular chamber of an eye. By way of example, the surgeon may remove a cataracteous lens, or reattach a retina with the instrument.

During a procedure, irrigation fluid is introduced into the eye to maintain the ocular pressure of the anterior chamber. The handpiece tip is coupled to an aspiration system that pulls the irrigation fluid and possibly tissue out of the anterior chamber. The tissue and irrigation fluid flow through an inner channel in the tip.

The aspiration system includes a pump coupled to an aspiration tube. The aspiration tube is connected to an outlet port of the handpiece. Most aspiration pumps are of the peristaltic type because the pump behavior is predictable. A peristaltic pump essentially pushes the air/fluid within the aspiration tube to create, a vacuum pressure within the tube. The operation of a peristaltic pump creates surges in the pressure within the system. Pressure surges can be undesirable when performing delicate procedures such as retinal reattachment.

Some aspiration systems contain a venturi type pump. Venturi pumps do not create pressure surges and are thus typically used in delicate ophthalmic procedures. Commercially available venturi pumps require a tank of compressed nitrogen gas. It is generally undesirable to have a pressurized gas tank in an operating environment. Additionally, venturi pumps are energy inefficient in creating a vacuum.

SUMMARY

According to one implementation, a pump for a medical aspiration system is provided. The pump includes a housing with an input port, an output port, a first cylinder and a second cylinder. A motor assembly of the pump moves a first plunger within the first cylinder and a second plunger within a second cylinder. The pump includes valve assemblies that control fluid communication between the input/output ports and the cylinders.

According to another implementation, a method for aspirating irrigation fluid from an eye is provided. Irrigation fluid is introduced into the eye. An aspiration instrument is inserted into the eye. The aspiration instrument communicates with a first aspiration tube. Irrigation fluid is aspirated from the eye, through the aspiration instrument and into the first aspiration tube by operating a vacuum pump to create a vacuum pressure in the first aspiration tube. The vacuum pump includes a first cylinder communicating with the first aspiration tube and with a second aspiration tube, and a second cylinder communicating with the first aspiration tube and the second aspiration tube. Operating the vacuum pump includes moving a first plunger between a suction stroke and a discharge stroke and moving a second plunger between a suction stroke and a discharge stroke. During the suction stroke of the first plunger, irrigation fluid flows from the first aspiration tube into the first cylinder. During the discharge stroke of the first plunger, irrigation fluid flows from the first plunger into the second aspiration tube. During the suction stroke of the second plunger, irrigation fluid flows from the first aspiration tube into the second cylinder. During the discharge stroke of the second plunger, irrigation fluid flows from the second plunger into the second aspiration tube. Respective fluid flows into and out from the first cylinder and into and out from the second cylinder are controlled by controlling respective positions of a first input valve interposed between the first aspiration tube and the first cylinder, a first output valve interposed between the first cylinder and the second aspiration tube, a second input valve interposed between the first aspiration tube and the second cylinder, and a second output valve interposed between the second cylinder and the second aspiration tube. The vacuum pressure in the first aspiration tube is adjusted to a desired vacuum pressure setting by manipulating an input of a control device. The vacuum pressure in the first aspiration tube is maintained at the desired vacuum pressure setting by controlling respective movement speeds and directions of the first plunger and the second plunger relative to each other, and controlling respective positions of the first input valve, the first output valve, the second input valve and the second output valve. The controlling is based on the desired vacuum pressure setting and measurements of respective pressures in the first cylinder and the second cylinder. The vacuum pressure in the first aspiration tube is maintained at the desired vacuum pressure setting while transitioning from the suction stroke of the first plunger to the suction stroke of the second plunger, by synchronizing respective positions of the first plunger, the second plunger, the first input valve, the first output valve, the second input valve and the second output valve, such that initiation of the suction stroke of the second plunger during the transitioning is delayed until a vacuum pressure in the second cylinder is equal to a vacuum pressure in the first cylinder.

According to another implementation, the method includes adjusting the vacuum pressure in the first aspiration tube to a new vacuum pressure setting by manipulating the control device. A pressure surge in the first aspiration tube is avoided during adjustment from the desired vacuum pressure setting to the new vacuum pressure setting, by synchronizing respective positions of the first plunger, the second plunger, the first input valve, the first output valve, the second input valve and the second output valve.

DETAILED DESCRIPTION

Disclosed is a dual cylinder pump that is used to create a vacuum in an aspiration tube of a medical system. The pump includes a first plunger that moves within a first cylinder and a second plunger that moves within a second cylinder. Movement of the plungers is controlled by a motor assembly. The pump includes valves that control the flow of fluid into and out of the cylinders so that one cylinder is pulling fluid from the aspiration tube while the other cylinder is discharging fluid. In this manner the pump is continuously pulling vacuum, thereby preventing vacuum surges found in peristaltic pumps of the prior art. Additionally, the pump is relatively energy efficient and does not require a separate nitrogen tank as required by commercially available venturi pumps of the prior art. The pump can be constructed as a cartridge that can be removed and disposed.

Figure 1:
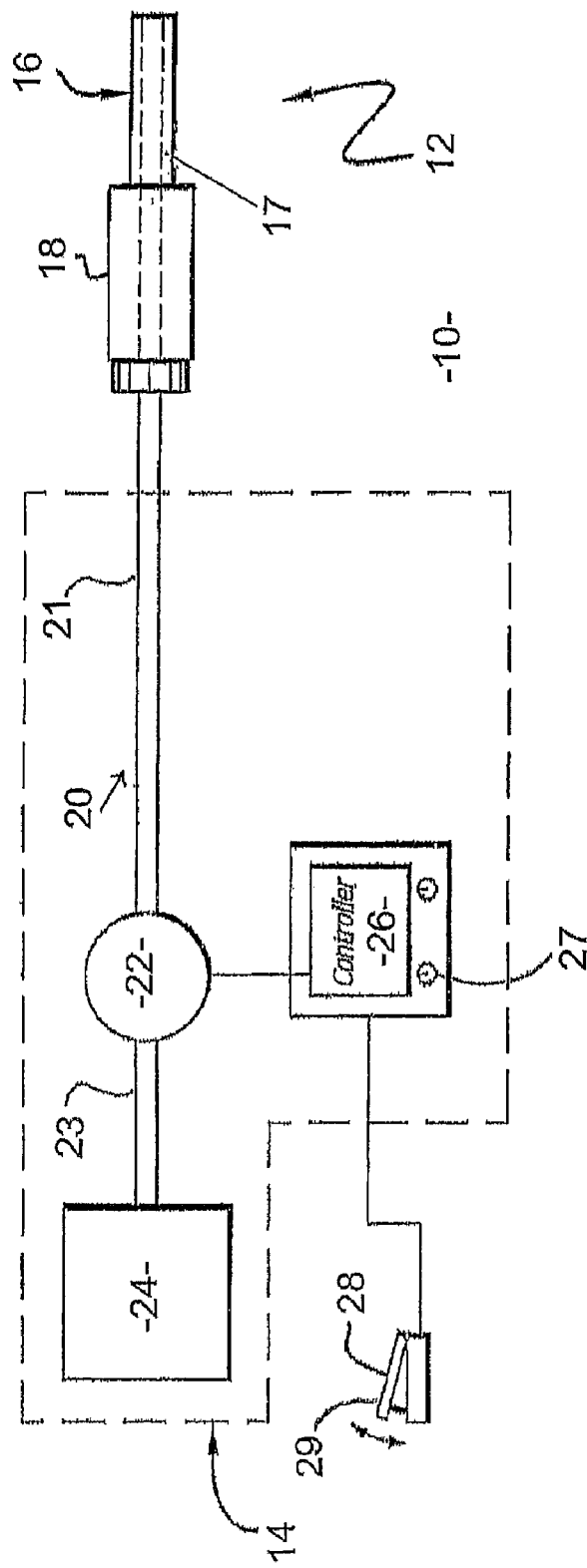
FIG. 1 is a schematic of an embodiment of a medical system.

Referring to the drawings more particularly by reference numbers, FIG. 1 shows an embodiment of a medical system 10 of the present invention. The system 10 may be used by a surgeon to perform ophthalmic medical procedures such as cataract lens removal, or retina reattachment.

The system 10 may include a surgical aspiration instrument 12 that is coupled to an aspiration system 14. The aspiration instrument 12 may include a tip 16 that extends from a handpiece 18 and can be held by a surgeon. The tip 16 can be inserted into the eye of a patient. The tip 16 is hollow and thereby defines an inner channel 17 through which irrigation fluid and possibly tissue may flow. Accordingly, the inner channel 17 extends through the tip 16 and, in the illustrated example, through the handpiece 18 to the rear of the handpiece 18 opposite to the tip 16.

The aspiration system 14 may include an aspiration line or conduit 20 that is coupled to the aspiration instrument 12. The aspiration line 20 is connected to a vacuum pump 22 and a collection canister 24. The vacuum pump 22 creates a vacuum pressure within the aspiration line 20 and a flow of fluid from the aspiration instrument 12 to the collection canister 24. The aspiration system 14 can pull (e.g., evacuate or aspirate) emulsified tissue and fluid from the aspiration instrument 12 and into the collection canister 24. In the illustrated example, the aspiration line 20 includes a first aspiration tube 21 fluidly interconnecting the inner channel 17 of the aspiration instrument 12 and the input side of the vacuum pump 22, and a second aspiration tube 23 fluidly interconnecting the output side of the vacuum pump 22 and the collection canister 24.

The system 10 may include one or more control devices. In the illustrated example, the system 10 includes a controller unit 26 that is connected to the aspiration instrument 12 and the vacuum pump 22. The system 10 may further include a foot pedal 28 that is connected to the controller unit 26. The surgeon can control the aspiration instrument 12 and/or the pump 22 by manipulating an input 27 or 29 of the controller unit 26 and/or the foot pedal 28, such as to adjust the vacuum pressure in the first aspiration tube 21 to a desired vacuum pressure setting and readjust the vacuum pressure to new settings as needed during a particular surgical procedure. The controller unit 26 may be an electronic controller and include a processor, memory, etc. (not shown) that can operate the pump 22 in synchronization with the aspiration instrument 12. Although the foot pedal 28 is shown as being connected to the controller unit 26, the foot pedal 28 may be connected directly to the pump 22 and/or aspiration instrument 12.

Figure 2:
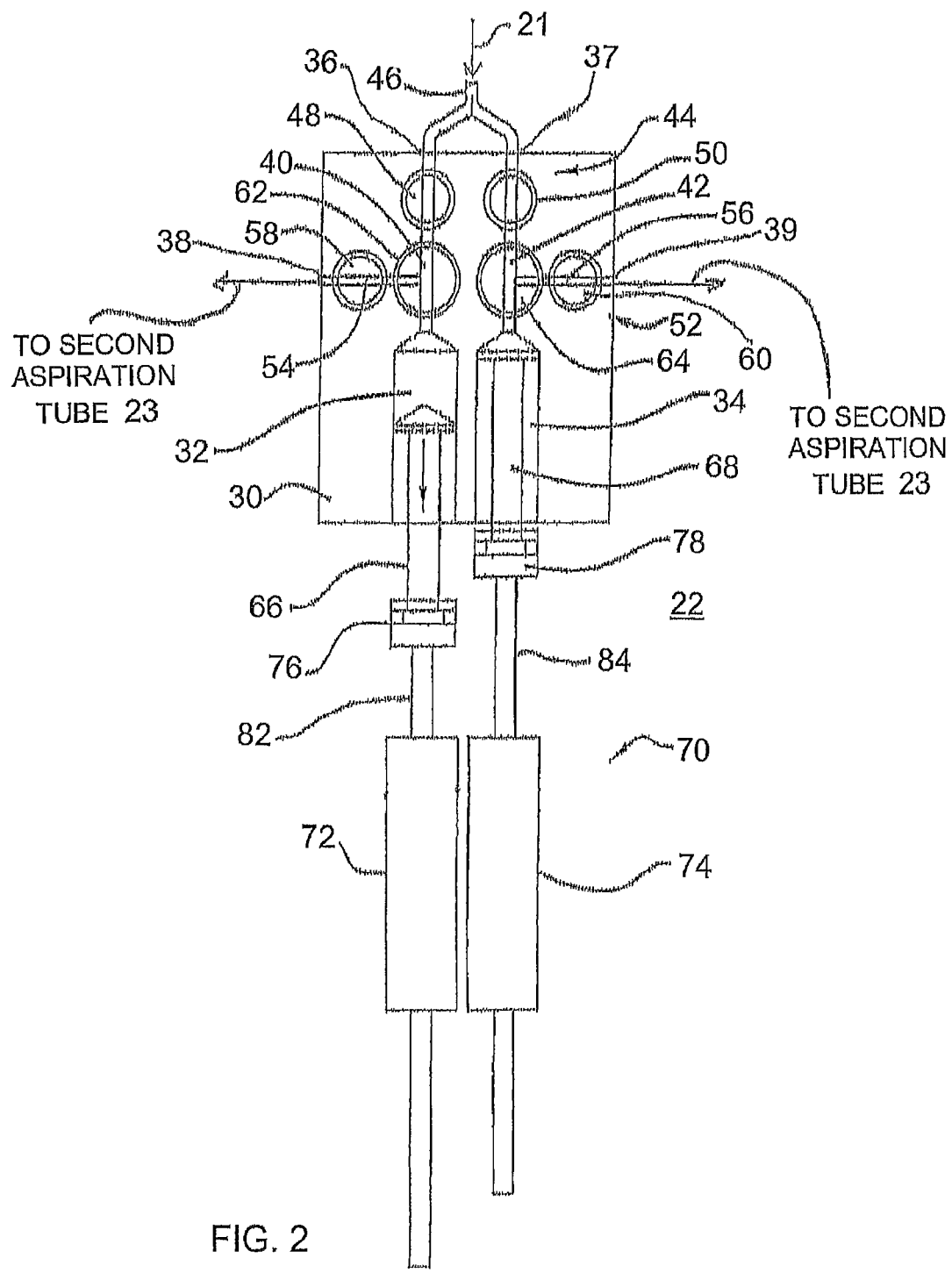
FIG. 2 is an illustration of a dual cylinder pump of the medical system.

FIG. 2 shows an embodiment of the vacuum pump 22. The pump 22 may include a housing 30 that has a first cylinder 32 and a second cylinder 34. The housing 30 also provides a fluid input and a fluid output. In the illustrated example, the fluid input includes a first input port 36 and a second input port 37, and the fluid output includes a first output port 38 and a second output port 39. A manifold tube 46 may be utilized to split the fluid flow from the first aspiration tube 21 into respective flows into the input ports 36 and 37. Thus, the first and second input ports 36 and 37 provide fluid communication from the first aspiration tube 21 (via the manifold tube 46) to the first and second cylinders 32 and 34, respectively. Likewise, the respective flows from the output ports 38 and 39 may be combined by a manifold tube (not shown) or otherwise connected to the second aspiration tube 23 in any suitable manner. Thus, the first and second output ports 38 and 39 provide fluid communication from the first and second cylinders 32 and 34, respectively, to the second aspiration tube 23. Also in the illustrated example, the housing 30 further includes inlet lines (channels, conduits, or the like) 40 and 42 in fluid communication with the first and second cylinders 32 and 34, respectively, and with the respective input ports 36 and 37. The housing 30 further includes outlet lines 54 and 56 in fluid communication with the first and second cylinders 32 and 34, respectively, and with the respective output ports 38 and 39.

The pump 22 may have a first valve assembly 44 that controls the flow of fluid into the first and second cylinders 32 and 34, from the first aspiration tube 21 and, in the illustrated example, via the input ports 36 and 37 and manifold tube 46. As previously noted, the manifold tube 46 is connected to the first aspiration tube 21 of the aspiration system 14 (FIG. 1). The first valve assembly 44 may include a first input valve 48 that interfaces with the first inlet line 40 to control the flow of fluid into the first cylinder 32, and a second input valve 50 that interfaces with the second inlet line 42 to control the flow of fluid into the second cylinder 34.

The pump 22 may further have a second valve assembly 52 that controls the flow of fluid from the first and second cylinders 32 and 34 and respectively through the outlet lines 54 and 56 of the housing 30. As previously noted, the outlet lines 54 and 56 are connected to the second aspiration tube 23 of the aspiration system 14 (FIG. 1) via the output ports 38 and 39. The second valve assembly 52 may include a first output valve 58 that interfaces with the first outlet line 38 to control the flow of fluid from the first cylinder 32, and a second output valve 60 that interfaces with the second outlet line 39 to control the flow of fluid from the second cylinder 34. The valves 48, 50, 58 and 60 may be controlled by actuators or motors that are connected to and controlled by the controller unit 26 shown in FIG. 1.

The pump 22 may include pressure transducers or sensors 62 and 64 that sense the pressure within the first and second cylinders 32 and 34, respectively. The pressure transducers 62 and 64 can be connected to the controller unit 26 shown in FIG. 1, and provide pressure feedback information that can be used in a feedback control loop of the pump 22.

The pump 22 includes a first plunger 66 that moves within the first cylinder 32 and a second plunger 68 that moves within the second cylinder 34. The plungers 66 and 68 are moved by a motor assembly 70. The motor assembly 70 may include a first motor or motor unit 72 that moves the first plunger 66 and a second motor or motor unit 74 that moves the second plunger 68. The motors 72 and 74 may move the plungers 66 and 68 out of phase relative to each other. By way of example, the plungers 66 and 68 may move 180 degrees out of phase relative to each other. The motors 72 and 74 may be connected to the controller unit 26 which controls the timing and phase of the plungers 66 and 68. Although two motors 72 and 74 are shown and described, it is to be understood that the plungers could be coupled to a single motor.

The motors 72 and 74 may be attached to the plungers 66 and 68 by couplers 76 and 78. The couplers 76 and 78 may be of the quick disconnect type so that the plungers 66 and 68 and the housing 30 can be detached from the motor assembly 70. This allows the housing 30 and plungers 66 and 68 to be packaged as a cartridge that can be detached after a medical procedure. The motor assembly 70 may include a first linkage 82 connected to the first plunger 66 and a second linkage 84 connected to the second plunger 68. Thus, during the operation of the motor assembly 70, movement of the first linkage 82 is translated into movement of the first plunger 66 alternately through its suction and discharge strokes, and movement of the second linkage 84 is translated into movement of the second plunger 68 alternately through its suction and discharge strokes. In the illustrated example, the first motor 72 is connected to the first linkage 82 and the second motor 74 is connected to the second linkage 84. In the illustrated example, the first linkage 82 is releasably connected to the first plunger 66 by the first coupler 76, and the second linkage 84 is releasably connected to the second plunger 68 by the second coupler 78. The plungers 66 and 68 may be of the syringe type that can be readily discarded and replaced. The housing 30 can be sterilized for reuse in the system 10. The valve actuators that actively control the valves 48, 50, 58 and 60 and the pressure transducers 62 and 64 may also be attached to the housing 30 in a sealed and readily detachable manner so that these components do not have to be sterilized after each procedure.

The controller unit 26 may control the motors 72 and 74 and the 20 valve assemblies 44 and 52 in the following manner. The first input valve 48 may be opened to provide fluid communication between the manifold tube 46 and the first cylinder 32. The second input valve 50 is closed. The first motor 72 may pull the first plunger 66 in a direction indicated by the arrow. Movement of the plunger 66 pulls fluid into the first cylinder 32.

When the first plunger 66 reaches an end of travel (suction stroke of first plunger 66), the first input valve 48 is closed and the second input valve 50 is opened. The second motor 74 then pulls the second plunger 68 to draw fluid into the second cylinder 34. During this second plunger movement the first motor 72 pushes the first plunger 66 (discharge stroke of first plunger 66). The first output valve 58 is opened so that the fluid within the first cylinder 32 is pushed out of the pump 22. The motors 72 and 74 and valves 48, 50, 58 and 60 are operated so that one of the cylinders 32 or 34 is pulling in fluid while the other cylinder 34 or 32 is pushing out fluid. In this manner a continuous vacuum is created in the aspiration line 20 (e.g., the first and second aspiration tubes 21 and 23). There are not sudden surges as found in prior art peristaltic pumps.

To maintain a continuous vacuum level, the second plunger 68 may begin to pull a vacuum in the second cylinder 34 as the first plunger 66 nears the end of travel in the first cylinder 32 during the discharge stroke of the first plunger 66. The second input valve 50 may be closed during movement of the second plunger 68 until the pressure transducers 62 and 64 sense the same pressure, wherein the second input valve 50 is opened and the first input valve 48 is closed.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although multiple valves 48, 50, and 60 are shown and described, it is to be understood that the pump 22 may have other valve arrangements. By way of example the pump 22 may have a single four-way valve.

What is claimed is:

1. A method for aspirating irrigation fluid from an eye, comprising:
   introducing irrigation fluid into the eye;
   inserting an aspiration instrument into the eye, the aspiration instrument communicating with a first aspiration tube;
   aspirating irrigation fluid from the eye, through the aspiration instrument and into the first aspiration tube by operating a vacuum pump to create a vacuum pressure in the first aspiration tube, the vacuum pump comprising a first cylinder communicating with the first aspiration tube and with a second aspiration tube, and a second cylinder communicating with the first aspiration tube and the second aspiration tube, wherein operating the vacuum pump comprises moving a first plunger between a suction stroke and a discharge stroke and moving a second plunger between a suction stroke and a discharge stroke, such that during the suction stroke of the first plunger irrigation fluid flows from the first aspiration tube into the first cylinder, during the discharge stroke of the first plunger irrigation fluid flows from the first plunger into the second aspiration tube, during the suction stroke of the second plunger irrigation fluid flows from the first aspiration tube into the second cylinder, and during the discharge stroke of the second plunger irrigation fluid flows from the second plunger into the second aspiration tube;
   controlling respective fluid flows into and out from the first cylinder and into and out from the second cylinder, by controlling respective positions of a first input valve interposed between the first aspiration tube and the first cylinder, a first output valve interposed between the first cylinder and the second aspiration tube, a second input valve interposed between the first aspiration tube and the second cylinder, and a second output valve interposed between the second cylinder and the second aspiration tube;
   adjusting the vacuum pressure in the first aspiration tube to a desired vacuum pressure setting by manipulating an input of a control device;
   maintaining the vacuum pressure in the first aspiration tube at the desired vacuum pressure setting by controlling respective movement speeds and directions of the first plunger and the second plunger relative to each other, and controlling respective positions of the first input valve, the first output valve, the second input valve and the second output valve, wherein controlling is based on the desired vacuum pressure setting and measurements of respective pressures in the first cylinder and the second cylinder; and
   maintaining the vacuum pressure in the first aspiration tube at the desired vacuum pressure setting while transitioning from the suction stroke of the first plunger to the suction stroke of the second plunger, by synchronizing respective positions of the first plunger, the second plunger, the first input valve, the first output valve, the second input valve and the second output valve, such that initiation of the suction stroke of the second plunger during the transitioning is delayed until a vacuum pressure in the second cylinder is equal to a vacuum pressure in the first cylinder.

2. The method of claim 1, wherein the irrigation fluid flowing into the first aspiration tube includes tissue removed from the eye.

3. The method of claim 2, comprising operating the aspiration instrument to remove the tissue from the eye.

4. The method of claim 1, wherein the fluid aspirated from the eye is an irrigation fluid.

5. The method of claim 1, wherein manipulating the input of the control device comprises operating a foot pedal.

6. The method of claim 1, comprising measuring the respective pressures in the first cylinder and the second cylinder by receiving pressure feedback information at the control device from a first pressure transducer communicating with the first cylinder and a second pressure transducer communicating with the second cylinder, respectively.

7. The method of claim 1, comprising adjusting the vacuum pressure in the first aspiration tube to a new vacuum pressure setting by manipulating the control device, and avoiding a pressure surge in the first aspiration tube during adjustment from the desired vacuum pressure setting to the new vacuum pressure setting by synchronizing respective positions of the first plunger, the second plunger, the first input valve, the first output valve, the second input valve and the second output valve.

8. The method of claim 1, wherein the control device communicates with a first motor and a second motor, and further comprising, prior to operating the vacuum pump, attaching the first plunger to the first motor at a first coupler and attaching the second plunger to the second motor at a second coupler.

9. The method of claim 7 comprising, after operating the vacuum pump, detaching the first plunger from the first motor at the first coupler and detaching the second plunger from the second motor at the second coupler.

10. The method of claim 8, comprising discarding the detached first coupler and the detached second coupler, and attaching a new first plunger to the first motor at the first coupler and attaching a new second plunger to the second motor at the second coupler.

11. The method of claim 1, wherein operating the vacuum pump comprises moving the first plunger and the second plunger out of phase with each other.

12. The method of claim 1, comprising delaying flowing the fluid from the first cylinder into the second aspiration tube until after the vacuum pressure in the second cylinder is equal to the vacuum pressure in the first cylinder.

13. The method of claim 12, wherein delaying flowing the fluid from the first cylinder into the second aspiration tube comprises delaying initiation of the discharge stroke of the first plunger.

14. The method of claim 12, comprising positioning the first output valve in a closed state during at least a portion of the suction stroke of the first plunger, and delaying flowing the fluid from the first cylinder into the second aspiration tube comprises delaying positioning the first output valve from the closed state to an opened state.

15. The method of claim 14, wherein delaying flowing the fluid from the first cylinder into the second aspiration tube further comprises delaying initiation of the discharge stroke of the first plunger.

\* \* \* \* \*